(12) United States Patent  
Harada et al.

(10) Patent No.: US 8,500,758 B2  
(45) Date of Patent: Aug. 6, 2013

(54) AUXILIARY DEVICE FOR A PUNCTURE NEEDLE

(75) Inventors: Hisataka Harada, Fukuroi (JP); Kazuhiro Koike, Fukuroi (JP); Mihoko Furukawa, Fukuroi (JP)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/207,655

(22) Filed: Aug. 11, 2011

(65) Prior Publication Data

US 2011/0295280 A1     Dec. 1, 2011

Related U.S. Application Data

(63) Continuation of application No. 12/033,221, filed on Feb. 19, 2008, now abandoned.

(30) Foreign Application Priority Data

Feb. 20, 2007   (JP) .................................. 2007-39175

(51) Int. Cl.  
*A61B 17/04*   (2006.01)

(52) U.S. Cl.  
USPC .......................................... 606/144; 606/139

(58) Field of Classification Search  
USPC ................ 248/74.1, 68.1; 606/130, 139, 144  
See application file for complete search history.

(56) References Cited

U.S. PATENT DOCUMENTS

| | | | |
|---|---|---|---|
| 2,012,776 A | 8/1935 | Roeder | |
| 4,775,121 A | 10/1988 | Carty | |
| 4,935,027 A | 6/1990 | Yoon | |
| 5,037,433 A | 8/1991 | Wilk et al. | |
| 5,052,396 A | 10/1991 | Wedel et al. | |
| 5,100,387 A | 3/1992 | Ng | |
| 5,123,914 A | 6/1992 | Cope | |

(Continued)

FOREIGN PATENT DOCUMENTS

| | | |
|---|---|---|
| DE | 2900265 A1 | 7/1980 |
| JP | 61205510 U | 12/1986 |

(Continued)

OTHER PUBLICATIONS

European Search Report regarding related application serial No. EP 08101093.6 dated Apr. 20, 2010—8 pgs.

(Continued)

*Primary Examiner* — Gregory Anderson  
(74) *Attorney, Agent, or Firm* — Lisa E. Winsor, Esq.

(57) ABSTRACT

An auxiliary device for a puncture needle allowing an easier manipulation of puncture needles as well as being capable of improving the suture stability. The auxiliary device for a puncture needle comprises a plate-shaped auxiliary device main body on the surface of which parallel guide grooves were formed, and a plate-shaped rotating-sliding contact part rotatably attached to one of the edge parts of the auxiliary device main body. Moreover, a stabilization plate was provided at the lower end part of the auxiliary device main body. And, a window part for confirming an insertion-puncture needle-outer needle and a pullout-puncture needle were provided at the lower part side portion of the auxiliary device main body. Moreover, a projecting edge part was formed at the upper end part of the auxiliary device main body, and an opening side width of a portion located at the projecting edge part of the guide grooves was made wider than the width of the other portion of the guide grooves.

9 Claims, 16 Drawing Sheets

U.S. PATENT DOCUMENTS

| | | | |
|---|---|---|---|
| 5,226,892 A | 7/1993 | Boswell | |
| 5,242,427 A | 9/1993 | Bilweis | |
| 5,251,873 A | 10/1993 | Atkinson et al. | |
| 5,281,237 A | 1/1994 | Gimpelson | |
| 5,330,488 A | 7/1994 | Goldrath | |
| 5,336,229 A | 8/1994 | Noda | |
| 5,336,231 A | 8/1994 | Adair | |
| 5,363,539 A | 11/1994 | Tisol | |
| 5,364,410 A | 11/1994 | Failla et al. | |
| 5,389,082 A | 2/1995 | Baugues et al. | |
| 5,391,182 A | 2/1995 | Chin | |
| 5,462,560 A | 10/1995 | Stevens | |
| 5,499,991 A | 3/1996 | Garman et al. | |
| 5,501,691 A | 3/1996 | Goldrath | |
| 5,531,699 A | 7/1996 | Tomba et al. | |
| 5,562,684 A | 10/1996 | Kammerer | |
| 5,626,590 A | 5/1997 | Wilk | |
| 5,643,295 A | 7/1997 | Yoon | |
| 5,653,716 A | 8/1997 | Malo et al. | |
| 5,665,096 A | 9/1997 | Yoon | |
| 5,681,333 A | 10/1997 | Burkhart et al. | |
| 5,722,981 A | 3/1998 | Stevens | |
| 5,741,276 A | 4/1998 | Poloyko et al. | |
| 5,782,845 A | 7/1998 | Shewchuk | |
| 5,795,335 A | 8/1998 | Zinreich | |
| 5,817,108 A | 10/1998 | Poncet | |
| 5,817,111 A | 10/1998 | Riza | |
| 5,895,395 A | 4/1999 | Yeung | |
| 5,897,563 A | 4/1999 | Yoon et al. | |
| 5,921,993 A | 7/1999 | Yoon | |
| 5,938,668 A | 8/1999 | Scirica et al. | |
| 5,993,434 A | 11/1999 | Dev et al. | |
| 6,022,360 A | 2/2000 | Reimels et al. | |
| 6,036,700 A * | 3/2000 | Stefanchik et al. | 606/144 |
| 6,066,146 A | 5/2000 | Carroll et al. | |
| 6,110,183 A | 8/2000 | Cope | |
| 6,113,068 A | 9/2000 | Ryan | |
| 6,113,611 A | 9/2000 | Allen et al. | |
| RE36,974 E | 11/2000 | Bonutti | |
| 6,156,056 A | 12/2000 | Kearns et al. | |
| 6,451,024 B1 | 9/2002 | Thompson et al. | |
| 6,500,184 B1 | 12/2002 | Chan et al. | |
| 6,524,317 B1 | 2/2003 | Ritchart et al. | |
| 6,629,534 B1 | 10/2003 | St. Goar et al. | |
| 6,638,286 B1 | 10/2003 | Burbank et al. | |
| 6,699,263 B2 | 3/2004 | Cope | |
| 7,090,690 B2 | 8/2006 | Foerster et al. | |
| 7,172,162 B2 | 2/2007 | Mizukoshi et al. | |
| 7,306,613 B2 | 12/2007 | Kawashima et al. | |
| 7,320,693 B2 | 1/2008 | Pollack et al. | |
| 7,625,386 B2 | 12/2009 | Abe et al. | |
| 7,647,122 B2 | 1/2010 | Chan et al. | |
| 7,731,726 B2 | 6/2010 | Belhe et al. | |
| 7,842,050 B2 | 11/2010 | Diduch et al. | |
| 7,918,868 B2 | 4/2011 | Marshall et al. | |
| 7,942,898 B2 | 5/2011 | Ewers et al. | |
| 2003/0004523 A1 | 1/2003 | Chan et al. | |
| 2003/0109883 A1 | 6/2003 | Matsuzaki et al. | |
| 2004/0039442 A1 | 2/2004 | St. Goar et al. | |
| 2004/0249393 A1 | 12/2004 | Weisel et al. | |
| 2004/0249395 A1 | 12/2004 | Mikkaichi et al. | |
| 2005/0288689 A1 | 12/2005 | Kammerer et al. | |
| 2006/0069398 A1 | 3/2006 | Suzuki et al. | |
| 2007/0118153 A1 | 5/2007 | Funamura et al. | |
| 2007/0179509 A1 | 8/2007 | Nagata et al. | |
| 2007/0282351 A1 | 12/2007 | Harada et al. | |
| 2008/0200931 A1 | 8/2008 | Harada et al. | |
| 2008/0228204 A1 | 9/2008 | Hamilton et al. | |
| 2008/0243147 A1 | 10/2008 | Hamilton et al. | |
| 2008/0255591 A1 | 10/2008 | Harada et al. | |
| 2008/0269781 A1 | 10/2008 | Funamura et al. | |
| 2009/0088778 A1 | 4/2009 | Miyamoto et al. | |
| 2009/0163939 A1 | 6/2009 | Mabuchi et al. | |
| 2009/0318939 A1 | 12/2009 | Funamura et al. | |

FOREIGN PATENT DOCUMENTS

| | | | |
|---|---|---|---|
| JP | 04226643 A | 8/1992 | |
| JP | 05161655 A | 6/1993 | |
| JP | 06024533 B2 | 4/1994 | |
| JP | 06044511 U | 6/1994 | |
| JP | 07328020 | 12/1995 | |
| JP | 2002336262 A | 11/2002 | |
| JP | 2005270332 A | 10/2005 | |
| JP | 2006025932 | 2/2006 | |
| JP | 2006025933 | 2/2006 | |
| JP | 2006025934 | 2/2006 | |
| JP | 2006151429 | 5/2006 | |
| JP | 2007039175 A | 2/2007 | |
| JP | 2008164032 | 7/2008 | |
| JP | 2004141646 A | 6/2010 | |
| WO | 9421178 A1 | 9/1994 | |
| WO | 9522932 A1 | 8/1995 | |
| WO | 03065903 A1 | 8/2003 | |
| WO | 2004006782 A1 | 1/2004 | |
| WO | 2007018520 A1 | 2/2007 | |

OTHER PUBLICATIONS

Office action issued Sep. 29, 2010 in related U.S. Appl. No. 12/033,221—7 pgs.

Response filed Dec. 10, 2010 to Office Action dated Sep. 29, 2010 from related U.S. Appl. No. 12/033,221—7 pgs.

Office action issued Mar. 2, 2011 in related U.S. Appl. No. 12/033,221—6 pgs.

Response filed Apr. 22, 2011 to Office Action dated Mar. 2, 2011 from related U.S. Appl. No. 12/033,221—7 pgs.

Advisory action issued May 20, 2011 in related U.S. Appl. No. 12/033,221—3 pgs.

Supplemental Response to Office Action dated Mar. 2, 2011 in response to Advisory action issued May 20, 2011 in related U.S. Appl. No. 12/033,221—7 pgs.

Advisory action issued Jul. 26, 2011 in related U.S. Appl. No. 12/033,221—3 pgs.

Office action issued May 2, 2011 in related U.S. Appl. No. 12/487,108—17 pgs.

Response filed Sep. 2, 2011 to Office Action dated May 2, 2011 from related U.S. Appl. No. 12/487,108—27 pgs.

Office action issued Nov. 28, 2011 in related U.S. Appl. No. 12/487,108—14 pgs.

* cited by examiner

AUXILIARY DEVICE FOR A PUNCTURE NEEDLE

CROSS REFERENCE TO RELATED APPLICATIONS

This application is a continuation application of and claims the benefit of priority under 35 U.S.C. 120 to U.S. application Ser. No. 12/033,221, filed Feb. 19, 2008 now abandoned, which claims priority to Japanese Patent Application No. 2007-39175, filed Feb. 20, 2007, the entirety of each of which is hereby incorporated by reference for all purposes.

FIELD OF THE INVENTION

The present invention relates to an auxiliary device for puncture needle used when plural puncture needles employed in suturing the sutured part consisting of an organ and the skin portion in a patient's body are used to puncture a patient's body.

BACKGROUND OF THE INVENTION

Traditionally, medical suturing devices comprising plural puncture needles have been used to suture and secure the sutured part in a patient's body, particularly the sutured part consisting of an organ and the skin portion. For example, the intragastrical administrations of fluid diet and/or liquid nutritional supplements using a gastrostomy tube to persons who are unable to take food from mouth by their own due to functional decline in old age and/or diseases have been practiced, wherein the gastrostomy tube is attached to a hole part formed in the patient's abdominal region. In the foregoing case, in order to correctly attach the gastrostomy tube to the patient, a method for preliminarily securing the abdominal wall A and the gastric wall using a medical suturing device has also been practiced (for example, see Unexamined Patent Publication S05-161655).

This medical suturing device comprises two (2) puncture needles installed in parallel, spaced with the use of a connecting plate having a pair of connecting holes and an insertion length adjusting plate having a pair of interdigitation holes, and prior to performing the suture, these two puncture needles are used to simultaneously puncture into the sutured part of the patient. Next, while one of puncture needles is threaded with surgical suture, the other puncture needle is threaded with an inner needle to which a loop body consisting of a wire at the tip part is connected, and then the inner needle is pulled out from the puncture needle with the surgical suture grabbed by the loop body in the patient's body. And, after pulling out the two puncture needles from the patient, both side portions of the surgical suture protruding outside the patient's body are tied up to complete the suturing process. Moreover, the tip part of the puncture needle into which the inner needle is inserted, is formed in curvature with the tip opening facing transversely, so that the loop body protrudes toward the outside while extending in the transverse direction when the inner needle is pushed into the inside of the puncture needle so as to be able to grab the surgical suture.

However, in the conventional medical suturing device, because of the two puncture needles being fixed to the connecting plate and the insertion length adjusting plate at the time of making a puncture, there exists a problem that if the two puncture needles are not appropriately positioned relative to one another, the positional relationship cannot be corrected in midstream. Consequently, there is a difficulty in manipulating the puncture needles at the time of making a puncture.

The present invention is made in an effort to address the foregoing problems, and the purpose is to provide an auxiliary device for a puncture needle capable of improving the suture stability while making the manipulation of the puncture needle easier.

SUMMARY OF THE INVENTION

In one aspect, the present invention is directed to an auxiliary device for puncture needle used when plural puncture needles employed in securing an organ to the skin portion with surgical suture make a puncture in the aforementioned skin portion through to the aforementioned organ. The auxiliary device comprises an auxiliary device main body, on the surface of which plural parallel guide grooves are formed so as to be able to install the plural puncture needles which are movable in the axial direction, and a rotating-sliding contact part slidingly contacting to the peripheral surface of the puncture needles installed in the guide grooves by being rotatably attached to one of the edges approximately parallel to the extending direction of the guide grooves in the auxiliary device main body and by rotating to the surface side of the auxiliary device main body.

DESCRIPTION OF FIGURE NOTATIONS

10 . . . Auxiliary device for puncture needle,
11 . . . Auxiliary device main body,
12 . . . Rotating-sliding contact part,
12a . . . Hinge connecting part,
13 . . . Stabilization plate,
14 . . . Window part,
15 . . . Projecting edge part,
16, 17 . . . Guide grooves,
16a, 17a . . . Wide grooves,
16b, 17b . . . Narrow grooves,
20 . . . insertion-puncture needle,
30 . . . pullout-puncture needle,
A . . . Abdominal wall, B . . . Gastric wall.

DETAILED DESCRIPTION

Figure 1:
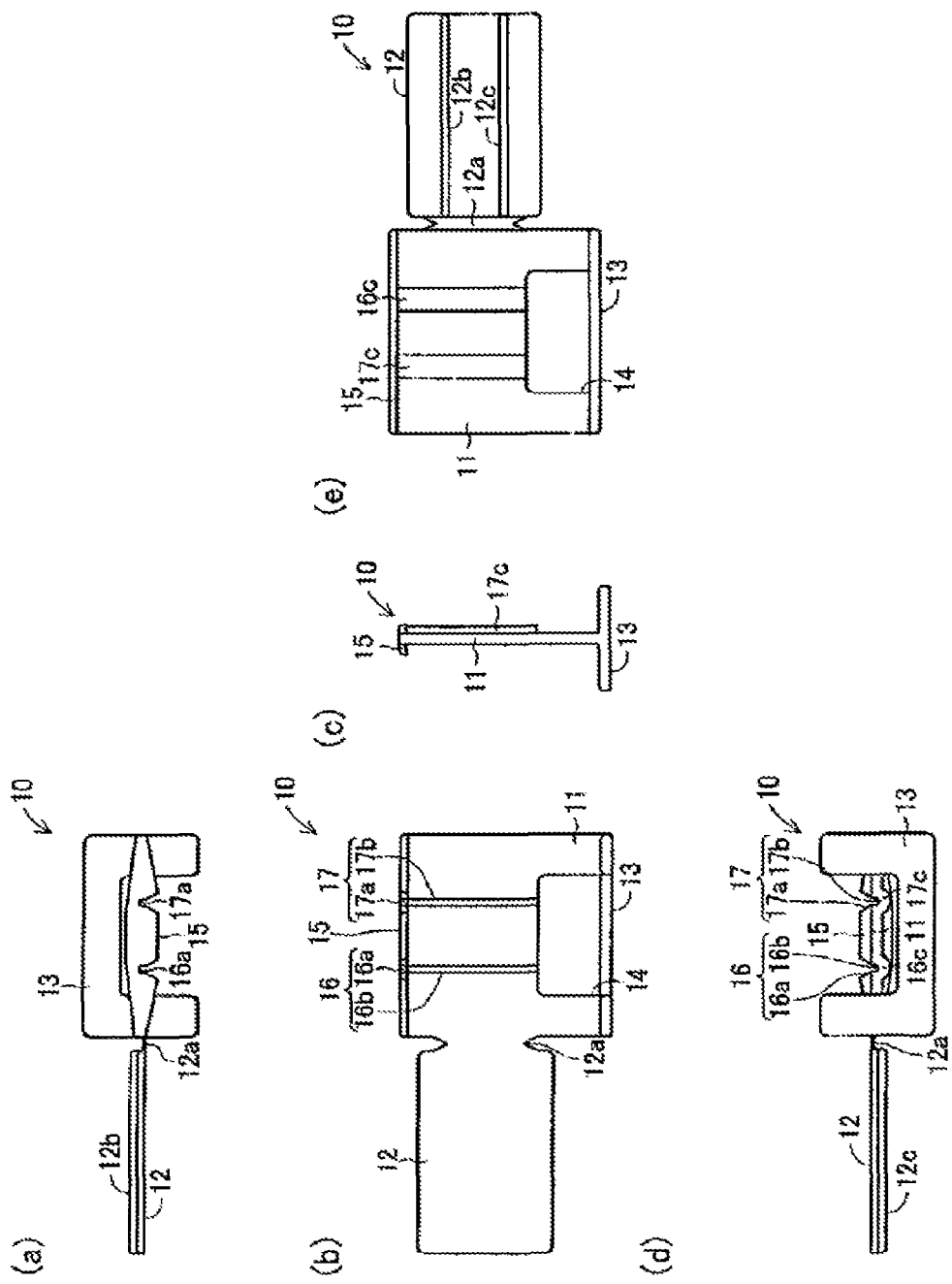
FIG. 1 shows the auxiliary device for puncture needle according to one embodiment of the present invention, in which (a) is a plane view, (b) is a front view, (c) is a side view, (d) is a bottom view and (e) is a rear view.

Hereinafter, one embodiment of this invention will be described with reference to the drawings. FIG. 1 shows an auxiliary device for puncture needle 10 according to the embodiment. This auxiliary device for puncture needle 10 comprises: a plate-shaped auxiliary device main body 11; a plate-shaped rotating-sliding contact part 12 rotatably connected to one of the edge parts of the auxiliary device main body 11, and a stabilization plate 13, which is a sideway U-shape in the plan view formed at the lower part of the auxiliary device main body 11, wherein, the auxiliary device main body 11 is formed in an approximately quadrangular shape with the length in the horizontal (right/left) direction being slightly longer than the length in the vertical (up/down) direction, on the centre lower part of which a rectangular window part 14, which is shorter in the vertical direction and longer in the horizontal direction than the auxiliary device main body 11, is formed.

Moreover, on the upper end part of the auxiliary device main body 11, as shown in FIG. 1(a), a spindle-shaped projecting edge part 15 with the width becoming wider in the centre side portion and narrower toward both ends in the plan view, is formed. On the surface of the auxiliary device main body 11, as shown in FIG. 1(b), a pair of guide grooves 16,17, which are extending from the projecting edge part 15 to the upper end part of the window part 14 in the vertical (up/down) direction, are formed from side to side keeping a certain distance. The guide grooves 16 comprise wide grooves 16a located on the surface of the projecting edge part 15 and narrow grooves 16b extending from the lower end part of the wide grooves 16a to the upper end part of the window part 14. The guide grooves 17 comprise wide grooves 17a located on the surface of the projecting edge part 15 and narrow grooves 17b extending from the lower end part of the wide grooves 17a to the upper end part of the window part 14.

Further, as shown in FIG. 1(d), the back side portion (the bottom side portion of the concave part) of the wide grooves 16a is formed in the identical shape with the narrow grooves 16b (a semicircle-shape in the plan view), and the opening side portion of the wide grooves 16a is formed in an approximately fan-shape with the width becoming gradually wider toward the outside. Similarly, the back side portion (the bottom side portion of the concave part) of the wide grooves 17a is formed in the identical shape with the narrow grooves 17b (a semicircle-shape in the plan view), and the opening side portion of the wide grooves 17a is formed in an approximately fan-shape with the width becoming gradually wider toward the outside. Moreover, as shown in FIG. 1(e), ribs 16c, 17c protruding toward the outside are formed at a position corresponding to the narrow grooves 16b, 17b in the back surface of the auxiliary device main body 11.

The rotating-sliding contact part 12 is formed in a rectangular-shape with the length in the horizontal (right/left) direction being approximately equal to the length in the horizontal direction of the auxiliary device main body 11, and the length in the vertical direction being approximately equal to the length between the lower end part of the projecting edge part 15 and the upper end of the window part 14 in the auxiliary device main body 11. This rotating-sliding contact part 12 is integrally formed with the auxiliary device main body 11 through the hinge connecting part 12a formed thin-walled, and rotates around the hinge connecting part 12a, allowing it to move forward/backward against the surface of the auxiliary device main body 11. Moreover, the rotating-sliding contact part 12 is connected to the auxiliary device main body 11 in such a manner that the upper end edge part thereof is positioned slightly lower side than the lower end part of the projecting edge part 15, and that the lower end edge part thereof is positioned slightly lower side than the upper end part of the window part 14. Ribs 12b, 12c extending to the right and left are formed on the back surface of the rotating-sliding contact part 12, keeping a certain distance in the vertical (up/down) direction.

The stabilization plate 13, which is connected to the lower end part of the auxiliary device main body 11 with the sideway U-shape opening side portion facing the front, is formed integrally with the auxiliary device main body 11 by connecting the lower end part of the auxiliary device main body 11 to approximately centre in the cross direction of both the right and left side portions respectively. Consequently, as shown in FIG. 1(a), (d), the guide grooves 16,17 formed at the auxiliary device main body 11 are positioned at the centre side of a sideway U-shape internal space of the stabilization plate 13 when viewed in the vertical (up/down) direction.

Figure 2:
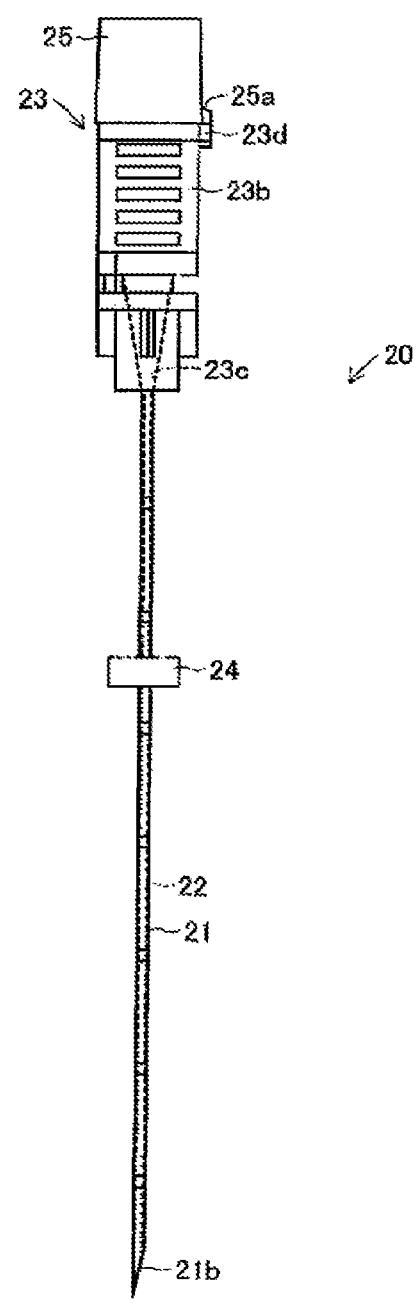
FIG. 2 is a front view showing an insertion-puncture needle.
Figure 3:
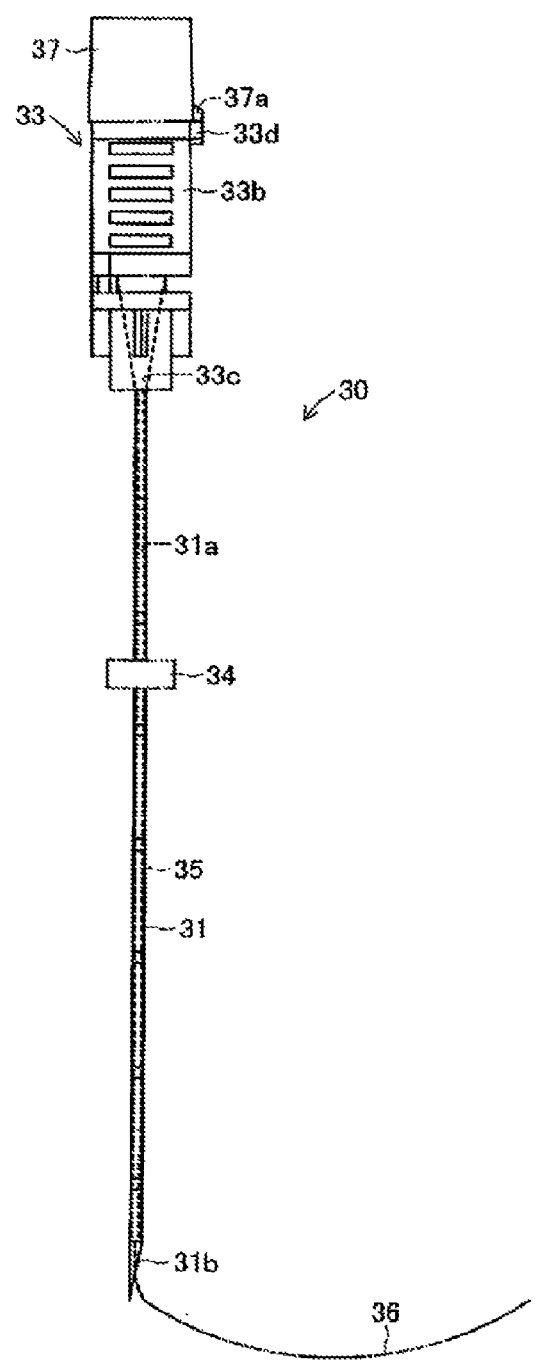
FIG. 3 is a front view showing a pullout-puncture needle.
Figure 4:
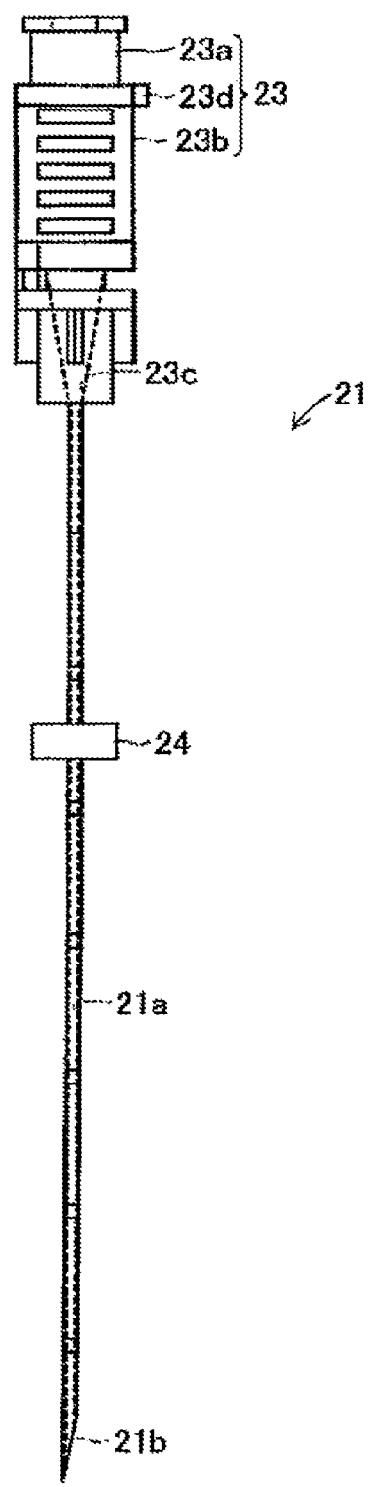
FIG. 4 is a front view showing an insertion-puncture needle-outer needle.
Figure 5:
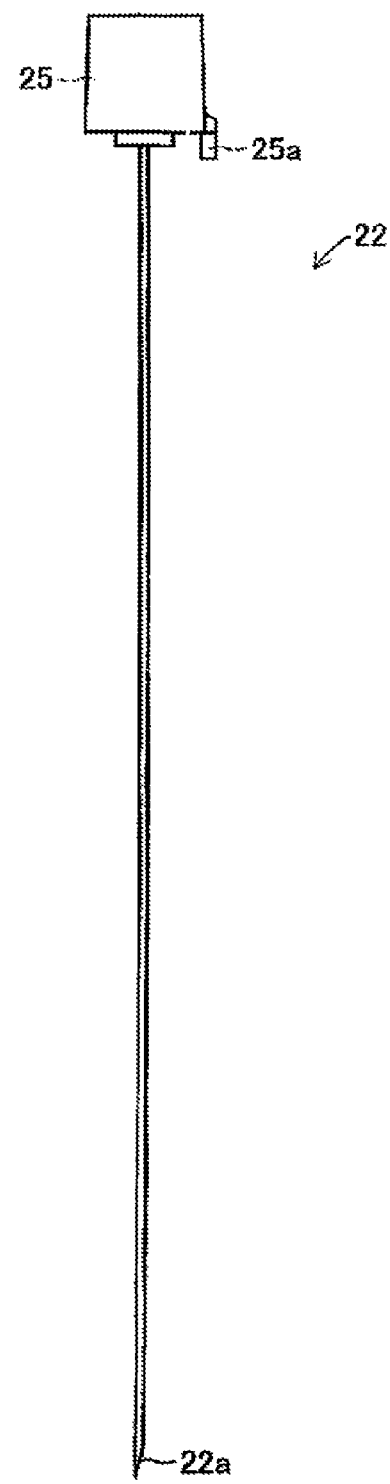
FIG. 5 is a front view showing an insertion-puncture needle-inner needle.

The auxiliary device for puncture needle 10 configured as the foregoing is used as an auxiliary device when the insertion-puncture needle 20 shown in FIG. 2, and the pullout-puncture needle 30 shown in FIG. 3, are used to puncture the patient's body. The insertion-puncture needle 20 comprises an insertion-puncture needle-outer needle 21 shown in FIG. 4, and an insertion-puncture needle-inner needle 22 shown in FIG. 5, wherein the insertion-puncture needle-outer needle 21 comprises a stainless steel cylindrical body, inside of which an insertion hole 21a for inserting the insertion-puncture needle-inner needle 22 is formed, and the resin-made hub part 23 is attached to the base part (the upper end part) thereof. On this hub part 23, an upper part 23a is formed in a small cylindrical shape and a hub main body 23b is formed in a rectangular tubular shape from the centre to lower part side with the width becoming wider than that of the upper part 23a, wherein a guide hole 23c communicating to the insertion hole 21a is formed in the inside of the hub part 23.

This guide hole 23c is formed in such a manner that the upper part side has a larger-diameter and the lower part side has a smaller-diameter, thereby the insertion-puncture needle-inner needle 22 can be inserted more easily from the upside of the hub part 23 and through the inside of the insertion hole 21a. Moreover, a circular engaged part 23d having a vertical (up/down) pass through hole part is provided at one of the upper end parts on the peripheral surface of the hub main body 23b. Additionally, a portion corresponding to the circular engaged part 23d in the tip part (lower end) of the insertion-puncture needle-outer needle 21 is cut off in an oblique direction, and is formed so that an opening 21b is visible from the transverse direction. More specifically, the opening 21b and the circular engaged part 23d are formed to face the same direction, and the facing direction of the opening 21b can be confirmed according to the position of the circular engaged part 23d.

A plate-shaped positioning part 24 is attached to the downside of the hub part 23 in the insertion-puncture needle-outer needle 21 spaced from the hub part 23. This positioning part 24 is attached to the insertion-puncture needle-outer needle 21 by inserting the insertion-puncture needle-outer needle 21 to the hole part formed at the centre part, and the attachment position thereof is arbitrarily setup in accordance with the projection amount (the sum of the length inserted to the suture part and the length in the vertical (up/down) direction of the auxiliary device for puncture needle 10) that is lower portion to the positioning part 24 of the insertion-puncture needle-outer needle 21.

The insertion-puncture needle-inner needle 22 comprises a stainless steel thin rod insertable into the inside of the insertion hole 21a of the insertion-puncture needle-outer needle 21, and a resin-made hub part 25 is attached to the base part (the upper end part). This hub part 25 is formed in a square pole shape, at the lower part side of which a concave part (not shown) capable of accommodating the upper part 23a of the hub part 23 is formed. Moreover, an engaging projection part 25a which is insertable into the inside of the hole part of the circular engaged part 23d is formed at one side in the peripheral surface lower end part of the hub part 25, and the lower end part of the engaging projection part 25a thereof is extending toward the downside. And, a portion corresponding to the engaging projection part 25a in the tip part (lower end) of the insertion-puncture needle-inner needle 22 is cut off in an oblique direction, and the facing direction of the cutting plane 22a can be confirmed according to the position of the engaging projection part 25a.

Figure 6:
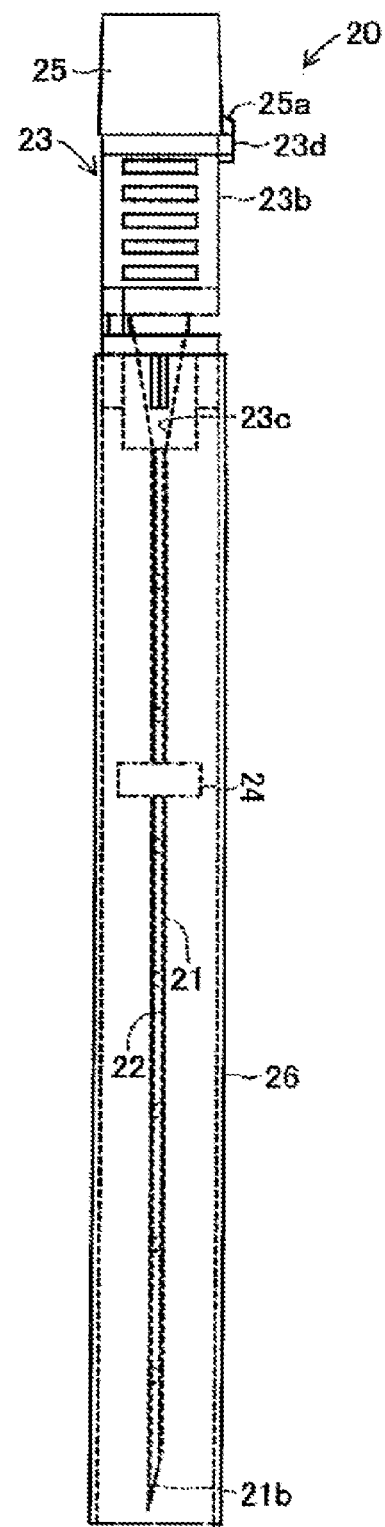
FIG. 6 is a front view showing an insertion-puncture needle to which a protector is attached.

Consequently, as the insertion-puncture needle-inner needle 22 is inserted into the inside of the insertion hole 21a of the insertion-puncture needle-outer needle 21, the upper part 23a of the hub part 23 is automatically set into the inside of the hub part 25 as shown in FIG. 2. At this time, the engaging projection part 25a is engaged with the circular engaged part 23d, and the cutting plane 22a of the insertion-puncture needle-inner needle 22 faces in the same direction as the opening 21b in the inside of the insertion hole 21a. Moreover, whenever the insertion-puncture needle 20, configured by assembling the insertion-puncture needle-inner needle 22 to the insertion-puncture needle-outer needle 21, is not in use, a cylindrical shape protector 26, which is shown in FIG. 6, is attached thereto. This protector 26 comprising a cylindrical body protects the puncture needle portion of the insertion-puncture needle 20 by engaging the lower end portion of the hub part 23 to the peripheral part of the opening, with the puncture needle portion of the insertion-puncture needle 20 being accommodated inside therein.

Figure 7:
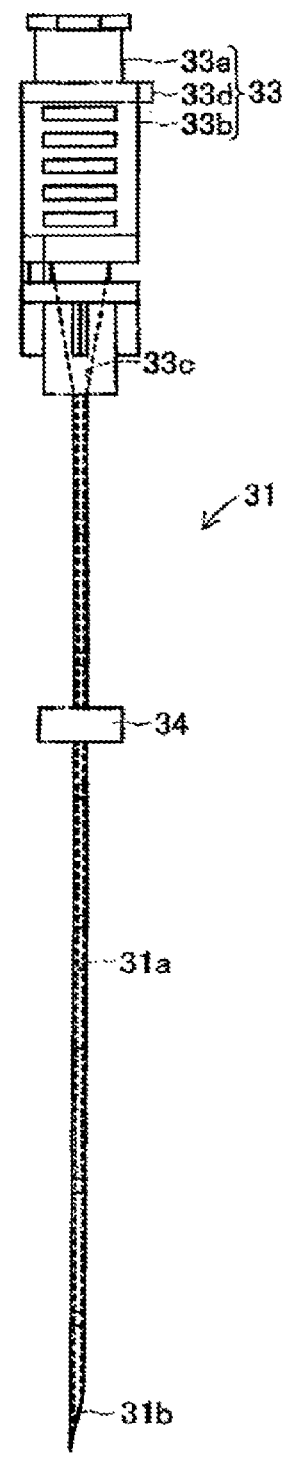
FIG. 7 is a front view showing a pullout-puncture needle-outer needle.
Figure 8:
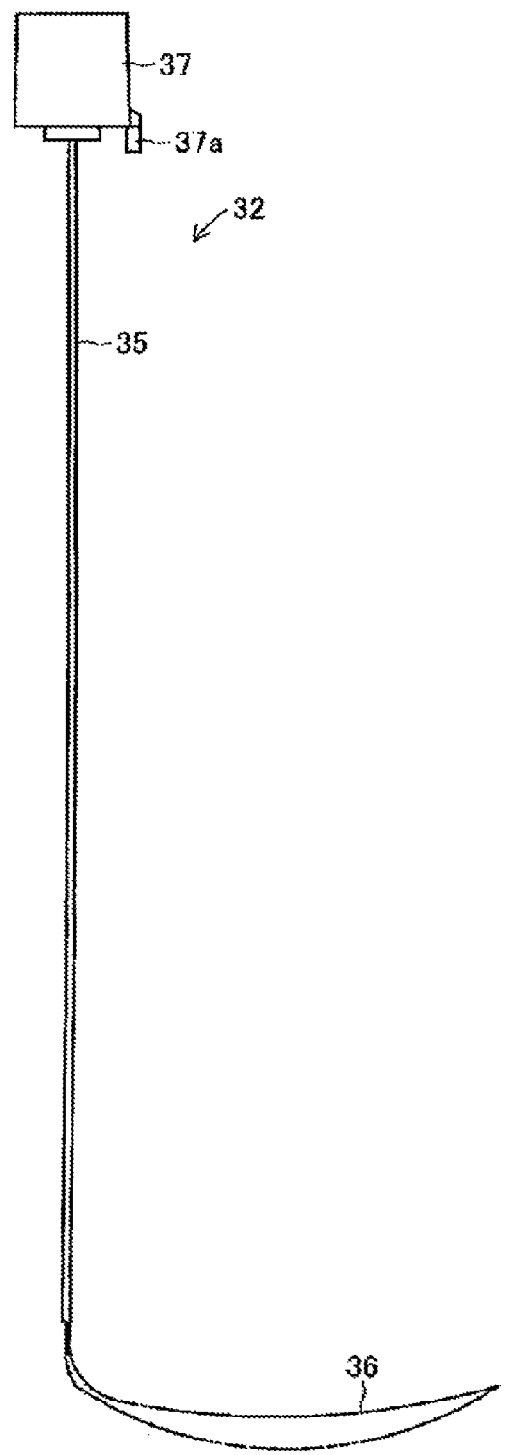
FIG. 8 is a front view showing a pullout-puncture needle-inner needle.

The pullout-puncture needle 30 comprises the pullout-puncture needle-outer needle 31 shown in FIG. 7 and the pullout-puncture needle-inner needle 32 shown in FIG. 8, wherein the pullout-puncture needle-outer needle 31 comprises a stainless steel cylindrical body, inside of which an insertion hole 31a for inserting the pullout-puncture needle-inner needle 32 is formed, and the resin-made hub part 33 is attached to the base part (the upper end part) thereof. On this hub part 33, an upper part 33a is formed in a small cylindrical shape and a hub main body 33b is formed in a rectangular tubular shape from the centre to lower part side with the width becoming wider than that of the upper part 33a, wherein a guide hole 33c communicating to the insertion hole 31a is formed in the inside of the hub part 33.

This guide hole 33c is formed in such a manner that the upper part side has a larger-diameter and the lower part side has a smaller-diameter, thereby the pullout-puncture needle-inner needle 32 can be inserted more easily from the upside of the hub part 33 and through the inside of the insertion hole 31a. Moreover, a circular engaged part 23d having a vertical pass through hole part is provided at one of the upper end parts on the peripheral surface of the hub main body 33b. Further, a portion corresponding to a circular engaged part 33d in the tip part (lower end) of the pullout-puncture needle-outer needle 31 is cut off in an oblique direction, and is formed so that an opening 31b is visible from the transverse direction. More specifically, the opening 31b and the circular engaged part 33d are formed to face the same direction, and the facing direction of the opening 31b can be confirmed according to the position of the circular engaged part 33d.

Figure 9:
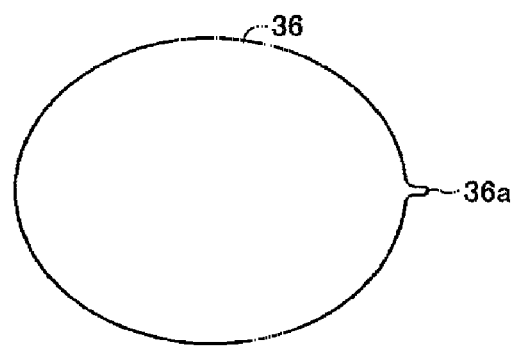
FIG. 9 is a plane view showing a capture part.

And a plate-shaped positioning part 34 is attached to the downside of the hub part 33 in the pullout-puncture needle-outer needle 31, spaced from the hub part 33. This positioning part 34 is attached to the pullout-puncture needle-outer needle 31 by inserting the pullout-puncture needle-outer needle 31 to the hole part formed at the centre part, the attachment position thereof is arbitrarily setup in accordance with the projection amount (the sum of the length inserted to the suture part and the length in the vertical (up/down) direction of the auxiliary device for puncture needle 10) that is lower portion to the positioning part 34 of the pullout-puncture needle-outer needle 31, The pullout-puncture needle-inner needle 32 comprises a thin stainless steel inner needle 35, now insertable into the inside of the insertion hole 31a of the pullout-puncture needle-outer needle 31; a circular capture part 36 provided at the tip part of the inner needle 35, and a hub part 37 provided at the upper end part of the inner needle 35. The capture part 36 comprises a very fine linear object which is thinner than the inner needle 35, and is bent from the tip part of the inner needle 35 extending in an approximately horizontal direction. This capture part 36 is in an approximately round shape in the plane view as shown in FIG. 9, and is in a circular arc shape in the side view with the centre portion being curved downward. A small U-shaped engaging curve part 36a is formed at the tip part of the capture part 36.

This capture part 36 is flexible and can be easily deformed into a straight line by applying a slight force so as to move away from the tip part of the engaging curve part 36a, and at the same time, the shape can be easily restored to the original circular shape by releasing the force. Moreover, a concave part (not shown) capable of accommodating the upper part 33a of the hub part 33 is formed at the lower part side portion of the hub part 37. Furthermore, an engaging projection part 37a insertable into the inside of the hole part of the circular engaged part 33d is formed at a portion corresponding to the extending direction of the capture part 36 in the peripheral surface lower end part of the hub part 37, and the lower end part of the engaging projection part 37a extends downward.

Figure 10:
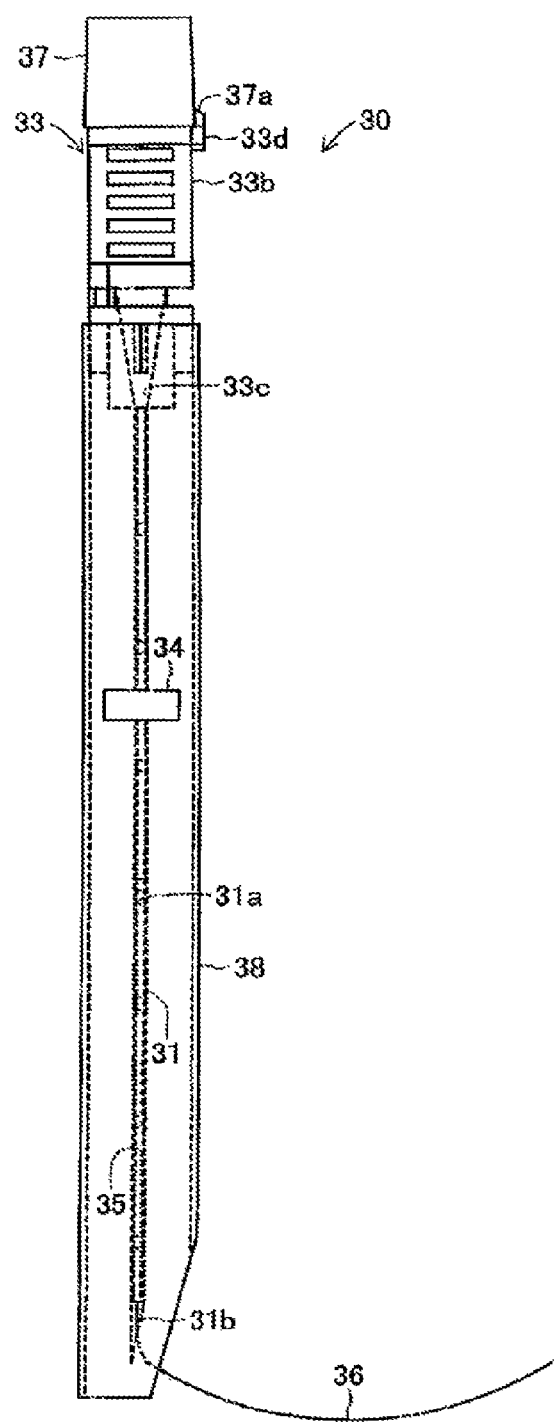
FIG. 10 is a front view showing a pullout-puncture needle to which a protector is attached.

Consequently, as the insertion-puncture needle-inner needle 32 is inserted into the inside of the insertion hole 31a of the insertion-puncture needle-outer needle 31 with the capture part 36 being extended in a straight line, the upper part 33a of the hub part 33 is automatically set into the inside of the hub part 35 as shown in FIG. 3. In this case, the engaging projection part 37a is engaged with the circular engaged part 33d, and the capture part 36 is protruded from the opening 31b of the pullout-puncture needle-outer needle 31 to the outside, returning to the circular shape. Moreover, whenever the pullout-puncture needle 30 configured by assembling the pullout-puncture needle-inner needle 32 to the pullout-puncture needle-outer needle 31 is not in use, an approximately cylindrical shape protector 36 shown in FIG. 10 is attached thereto.

This protector 38 comprises a tubular object, one side portion of the peripheral surface tip part of which is cut off obliquely so as to be opened together with the tip part, and the lower end portion of the hub part 33 is engaged to the peripheral part of the opening with the puncture needle portion of the pullout-puncture needle 30 being accommodated inside, thereby the puncture needle portion of the pullout-puncture needle 30 is protected. This configuration allows the capture part 36 to protrude from the tip side of the protector 38 so that no external force is applied to the capture part 36. Thus, the shape of the capture part 36 can be maintained for a long-term.

Figure 11:
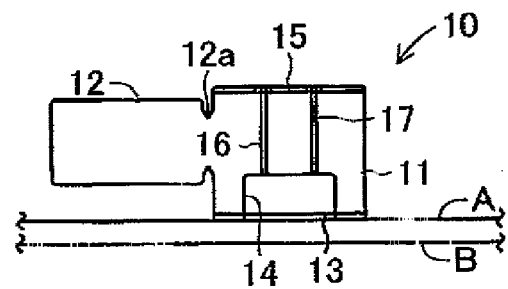
FIG. 11 is an illustration showing an auxiliary device for puncture needle installed in an abdominal region.
Figure 12:
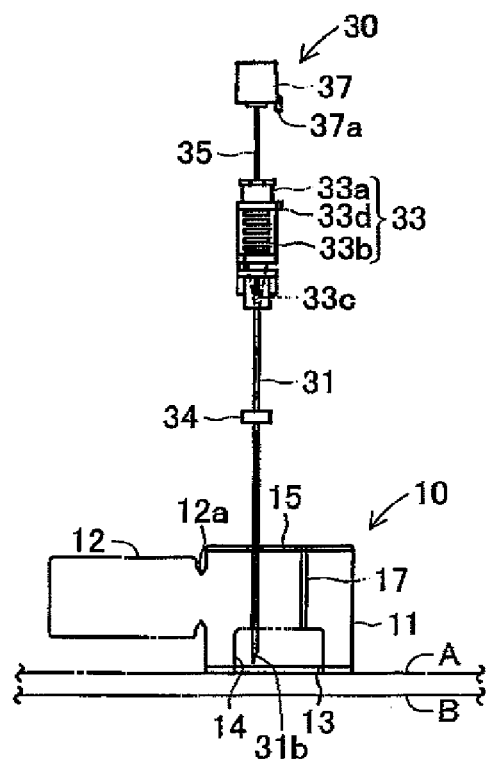
FIG. 12 is an illustration showing an auxiliary device for puncture needle, to the guide grooves of which a pullout-puncture needle is attached.

Next, the aforementioned auxiliary device for puncture needle 10, the insertion-puncture needle 20 and the pullout-puncture needle 30 are used to describe an exemplary case in which the abdominal wall A as the skin portion in an embodiment of this invention and the gastric wall B as the organ wall part of this invention (see FIG. 11 or FIG. 22) in a patient are sutured. In this suture, firstly, the auxiliary device for puncture needle 10 as shown in FIG. 11 is installed on the skin surface of the abdominal wall A in the patient. After that, the capture part 36 is accommodated inside of the pullout-puncture needle-outer needle 31, the tip side portion of the pullout-puncture needle 30 with the hub part 37 positioned at the upside of the hub part 33 of the pullout-puncture needle-outer needle 31 is inserted into the inside of the guide grooves 16 of the auxiliary device for puncture needle 10 as shown in FIG. 12.

Figure 13:
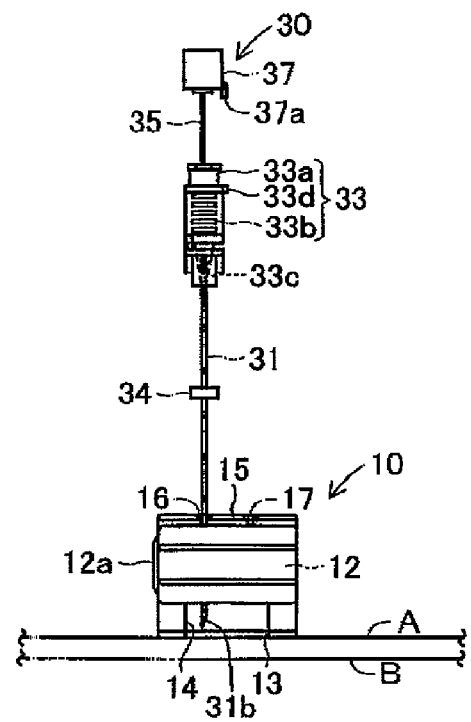
FIG. 13 is an illustration showing a rotating-sliding contact part rotated to the surface side of an auxiliary device main body.
Figure 14:
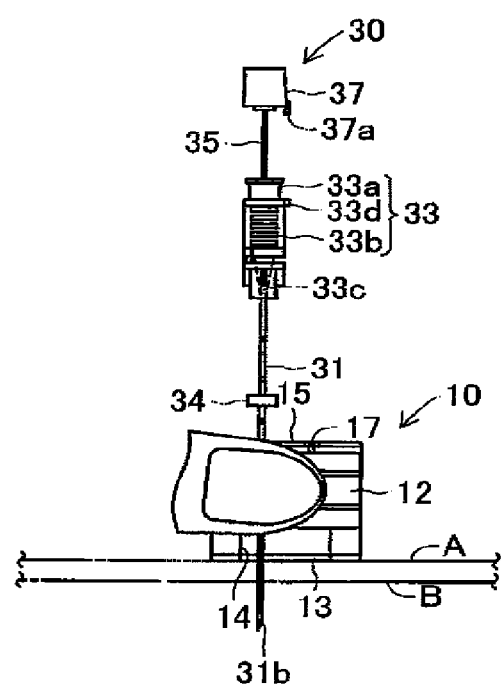
FIG. 14 is an illustration showing a pullout-puncture needle pierced into an abdominal region.

Next, the auxiliary device for puncture needle 10, the rotating-sliding contact part 12 is rotated to the surface side of the auxiliary device main body 11, and as shown in FIG. 13, the rotating-sliding contact part 12 is placed over the surface of the auxiliary device main body 11, and then the pullout-puncture needle 30 is pushed into the skin surface in the patient's abdominal region, and as shown in FIG. 14, the pullout-puncture needle 30 is pierced into the abdominal wall A and the gastric wall B. In this case, the rotating-sliding contact part 12 is pushed toward the auxiliary device main body 11 with fingers, thereby the pullout-puncture needle 30 is lowered while slidingly contacting the guide grooves 16 and the rotating-sliding contact part 12, with it being prevented from disengaging from the guide grooves 16 by the rotating-sliding contact part 12. Moreover, at that time, the puncturing state of the pullout-puncture needle 30 can be confirmed from the window part 14.

Figure 15:
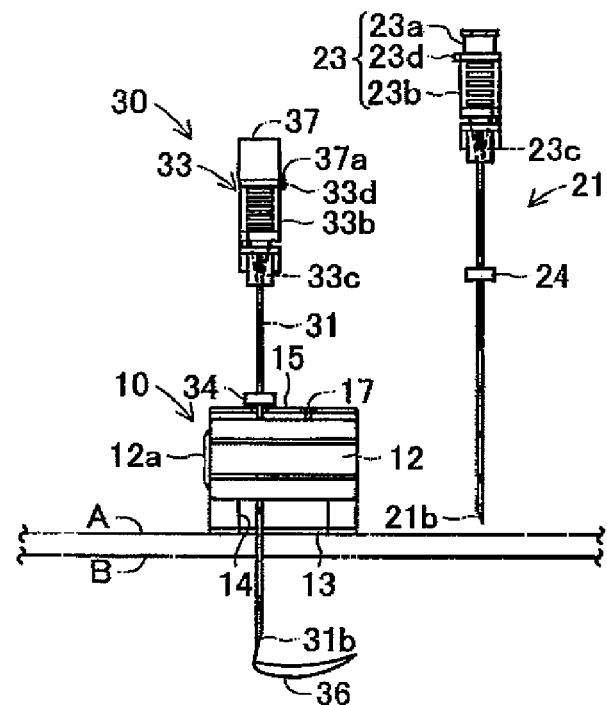
FIG. 15 is an illustration showing a capture part expanded to a circular shape inside the stomach.

In this case, the pullout-puncture needle 30 is pierced until the positioning part 34 runs into the upper end part of the auxiliary device for puncture needle 10 so that the opening 31b of the pullout-puncture needle-outer needle 31 is positioned at the inside of the gastric wall B. After that, while the engaging projection part 37a is being engaged to the circular engaged part 33d, the pullout-puncture needle-inner needle 32 is further inserted inside the pullout-puncture needle-outer needle 31, and as shown in FIG. 15, and allows the capture part 36 to protrude from the opening 31b of the pullout-puncture needle-outer needle 31. Thereby, the capture part 36 is spread to form a circular shape so as to be an approximately right angle to the pullout-puncture needle-outer needle 31 at the inside of the gastric wall B. The direction to which this capture part 36 spreads can be confirmed from the positions of the engaging projection part 37a and the circular engaged part 33d.

Figure 16:
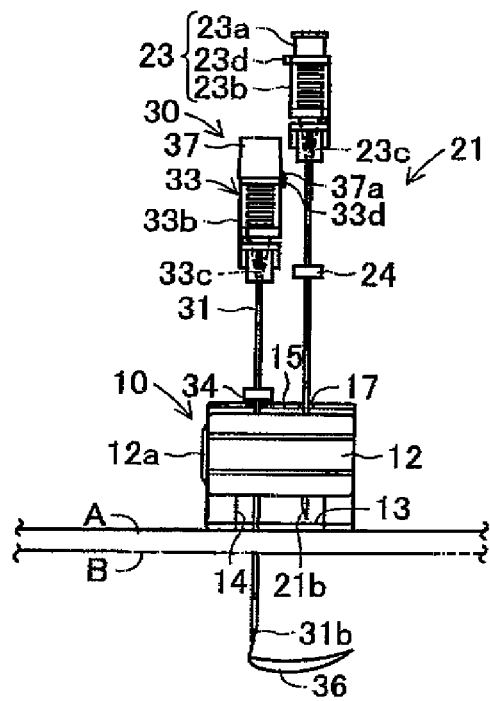
FIG. 16 is an illustration showing an auxiliary device for puncture needle, to which an insertion-puncture needle-outer needle is attached.

Then, the insertion-puncture needle 20 is pulled out from the insertion-puncture needle-inner needle 22, and the tip side portion of the insertion-puncture needle-outer needle 21 is inserted in between the guide grooves 17 of the auxiliary device for puncture needle 10 and the rotating-sliding contact part 12 as shown in FIG. 16. In this case, the upper end part of the guide grooves 17 comprises the wide grooves 17a, the wide which is wider at the open side, allowing the insertion-puncture needle-outer needle 21 to be attached easier. Moreover, in stead of these operations, with the rotating-sliding contact part being rotated once to expose the surface of the auxiliary device main body 11, the tip side portion of the insertion-puncture needle-outer needle 21 may be installed inside the guide grooves 17, and thereafter, the rotating-sliding contact part 12 may be rotated to the surface side of the auxiliary device main body 11 as well.

Figure 17:
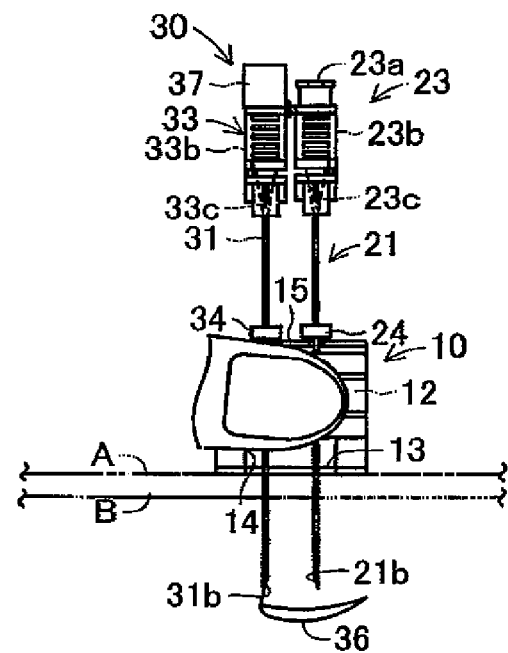
FIG. 17 is an illustration showing an insertion-puncture needle-outer needle pierced into an abdominal region.

After that, the insertion-puncture needle-outer needle 21 is pushed into the skin surface in the patient's abdominal region, and then pierced into the abdominal wall A and the gastric wall B. In this embodiment, as shown in FIG. 17, the insertion-puncture needle-outer needle 21 is pierced until the positioning part 24 runs into the upper end part of the auxiliary device for puncture needle 10, thereby the tip part of the insertion-puncture needle-outer needle 21 is positioned the centre neighborhood of the capture part 36. At this time, the circular engaged part 23d is made to face with the engaging projection part 37a and the circular engaged part 33d. Thereby, the opening 21b of the insertion-puncture needle-outer needle 21 is faced with the opening 31b of the pullout-puncture needle-outer needle 31.

Figure 18:
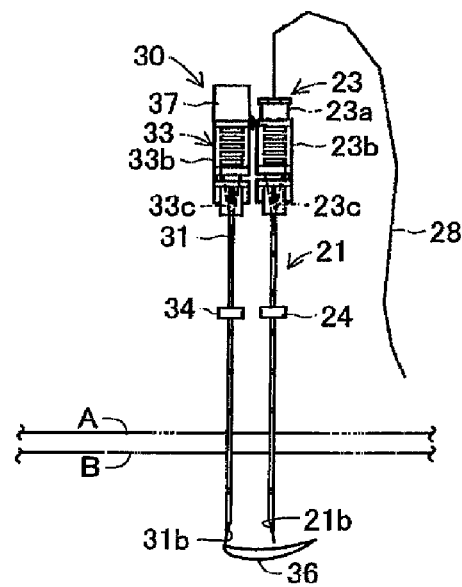
FIG. 18 is an illustration showing a surgical suture inserted into the inside of an insertion-puncture needle-outer needle.
Figure 19:
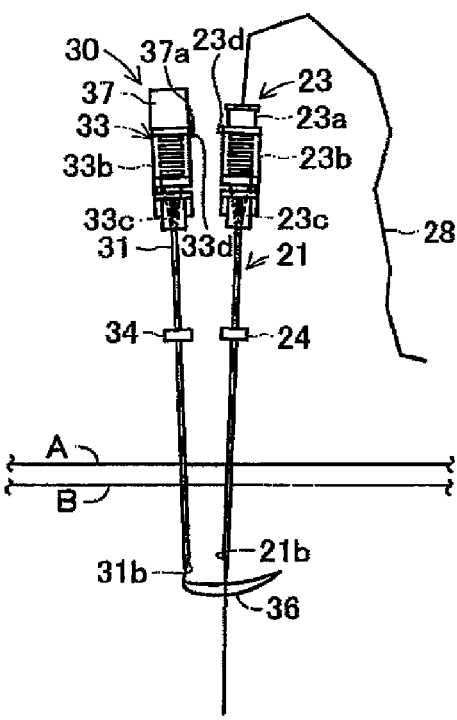
FIG. 19 is an illustration showing the tip part of a surgical suture threaded inside the capture part.
Figure 20:
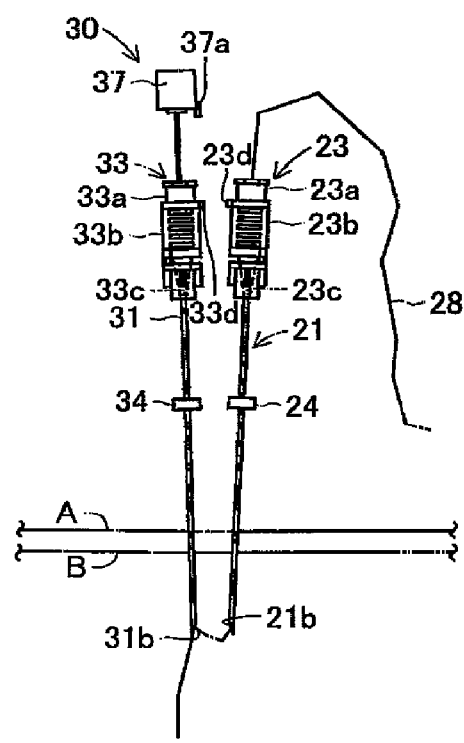
FIG. 20 is an illustration showing the tip side portion of a surgical suture engaged to the opening edge part of a pullout-puncture needle.

Then, after removing the auxiliary device for puncture needle 10 from the insertion-puncture needle-outer needle 21 and the pullout-puncture needle 30, as shown in FIG. 18, a surgical suture 28 is inserted from the guide hole of the hub part 23 into the inside of the insertion hole 21a, and allow the tip part thereof to protrude from the opening 21b of the insertion-puncture needle-outer needle 21 ad shown in FIG. 19. In this embodiment, while observing the tip portion of the surgical suture 28 and the capture part 36 with an endoscope, the tip portion of the surgical suture 28 is positioned inside the capture part 36 by arbitrarily manipulating the insertion-puncture needle-outer needle 21 or the tip part of the pullout-puncture needle 30. Next, as shown in FIG. 20, the hub part 37 is pulled upward to move the pullout-puncture needle-inner needle 32 to the upper part side of the pullout-puncture needle-outer needle 31.

Figure 21:
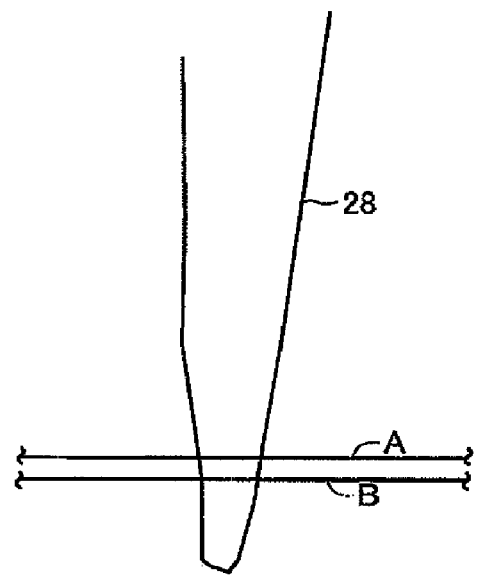
FIG. 21 is an illustration showing a surgical suture, both the end side portions of which are protruding out from an abdominal wall.

At this time, the tip portion of the surgical suture 28 is engaged with the capture part 36 trying to get inside the pullout-puncture needle-outer needle 31 together with the capture part 36 and pushed against the edge part of the opening 31b. Thereby, the tip portion of the surgical suture 28 is engaged to the edge part of the opening 31b. In the foregoing embodiment, by pulling out the insertion-puncture needle-outer needle 21 and the pullout-puncture needle 30 from the patient's body, both the end side portions of the surgical suture 28 pass completely through the gastric wall B and the abdominal wall A and protruded outside the patient's body, as shown in FIG. 21.

Figure 22:
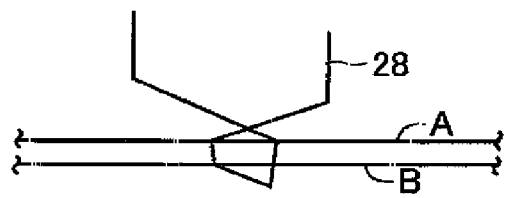
FIG. 22 is an illustration showing both the end side portions of a surgical suture protruded out from an abdominal wall to be tied together.

And, as shown in FIG. 22, both end side portions of the surgical suture 28 are tied, thereby the suturing process is finished. Incidentally, when inserting the surgical suture 28 into the inside of the insertion hole 21a of the insertion-puncture needle-outer needle 21, in the event that the surgical suture 28 gets stuck inside the insertion hole 21a, the surgical suture 28 can be pulled out from the insertion-puncture needle-outer needle 21 once, and the insertion-puncture needle-inner needle 22 can be inserted inside the insertion hole 21a to remove the suture stuck inside the insertion hole 21a, and then, the surgical suture 28 is inserted again into the inside of the insertion hole 21a to allow the tip side portion of the surgical suture 28 to protrude from the opening 21b.

As described above, in this auxiliary device for puncture needle 10, when the pullout-puncture needle 30 is used to puncture the patient's body with the tip portion of the puncture needle installed at the guide grooves 16 of the auxiliary device for puncture needle placed on the sutured part of the patient's body, the rotating-sliding contact part 12 is rotated to the surface side of the auxiliary device main body 11, thereby the pullout-puncture needle 30 can be prevented from disengaging from the guide grooves 16. And, the pullout-puncture needle 30 in the foregoing state is pushed toward the patient's body, thereby the tip part of the pullout-puncture needle 30 can make a puncture in the patient's body. In this case, since the pullout-puncture needle 30 moves along the guide grooves 16, the needle can puncture into the body in the appropriate state without displacement.

Moreover, in the event that the insertion-puncture needle-outer needle 21 is used to puncture the patient's body in parallel to the pullout-puncture needle 30, the tip side portion of the insertion-puncture needle 20 is inserted into the inside of the guide grooves 17 from the upper part side of the auxiliary device for puncture needle 10. Alternatively, with the rotating-sliding contact part 12 being moved away once from the surface of the auxiliary device main body 11, the tip side portion of the insertion-puncture needle-outer needle 21 is installed at the guide grooves 17, and the rotating-sliding contact part 12 is again rotated to the surface side of the auxiliary device main body 11, thereby the insertion-puncture needle-outer needle 21 can be prevented from disengaging from the guide grooves 17. And, the insertion-puncture needle-outer needle 21 in the foregoing state is pushed toward inside the patient's body, thereby a puncture can be made in the patient's body. In this case, since the insertion-puncture needle-outer needle 30 moves along the guide grooves 17, the needle can puncture into the body in the appropriate state without displacement.

Furthermore, in the event that the positional relationship between the pullout-puncture needle 30 and the insertion-puncture needle-outer needle 21 is not appropriate, the auxiliary device for puncture needle 10 can be removed to move the pullout-puncture needle 30 or the tip portion of the insertion-puncture needle-outer needle 21, so that the positional relationship one another can be adjusted so as to be in the positional relationship in which the surgical suture 28 and the capture part 36 are easily engaged. In addition, the auxiliary device main body 11 and the rotating-sliding contact part 12 are formed in a plate-shape, and the guide grooves 16,17 are formed from the upper end of the auxiliary device main body 11 to the upper end of the window part 14, thereby the auxiliary device main body 11 and the rotating-sliding contact part 12 can be easily grasped, making the manipulation easier. Moreover, the length of the guide grooves 16,17 are formed longer in the vertical (up/down) direction, and thereby the puncture operation is stabilized when making punctures using the pullout-puncture needle 30 and the insertion-puncture needle-outer needle 21.

In addition, the stabilization plate 13 was provided at the lower part of the auxiliary device main body 11, thereby the skin surface and the guide grooves 16,17 are perpendicularly intersected with one another when placing the stabilization plate 13 to the skin surface of the patient during the installation of the auxiliary device for puncture needle 10 in the patient's body. Consequently, the pullout-puncture needle 30 and the insertion-puncture needle-outer needle 21 can puncture the abdominal wall A and the gastric wall B of the patient at an appropriate angle. Moreover, the projecting edge part 15 was formed at the upper end part of the auxiliary device main body 11, and the wide grooves 16a, 17a were formed at the projecting edge part 15, thereby the projecting edge part 15 can act as a reinforcing part, enhancing the strength of the auxiliary device for puncture needle 10.

In addition, the opening side portion width of the wide grooves 16a,17a is wider, thereby the pullout-puncture needle 30 and the insertion-puncture needle-outer needle 21 can be attached to the guide grooves 16,17 more easily. Particularly, with the rotating-sliding contact part 12 being positioned to the surface side of the auxiliary device main body 11, the operation to insert the pullout-puncture needle 30 and the tip side portion of the insertion-puncture needle-outer needle 21 in between the guide grooves 17 of the auxiliary device for puncture needle 10 and the rotating-sliding contact part 12 is easier. Moreover, the window part 14 is provided at the lower part the auxiliary device main body 11, thereby the manipulation can be done while observing the pullout-puncture needle 30 passing through inside the auxiliary device for puncture needle 10 and the insertion-puncture needle-outer needle 21, allowing the operation to be more secure.

Moreover, the auxiliary device for puncture needle according to the present invention is not limited to the aforementioned embodiment, and may be optionally modified and implemented accordingly within the scope of the invention. For example, in the aforementioned embodiment, although the auxiliary device main body 11 is formed in a thin plate body, this auxiliary device main body may also be configured using a thick plate body, through the use of which the stabilization plate 13 and the projecting edge part 15 may be omitted. Moreover, the window part 14 provided at the auxiliary device for puncture needle 10 may also be omitted. In this case, the puncture needles can be manipulated while observing the pullout-puncture needle 30 protruding out of the lower end part of the rotating-sliding contact part 12 and the tip portion of the insertion-puncture needle-outer needle 21. Moreover, the length of the rotating-sliding contact part 12 in the vertical (up/down) direction may also be extended to arrange the window part at the lower part of the rotating-sliding contact part.

In addition, in the aforementioned embodiment, although only a pair of guide grooves 16,17 are formed on the auxiliary device main body 11, 3 or more of these guide grooves may also be formed. This allows, the distance between the pullout-puncture needle 30 and the insertion-puncture needle-outer needle 21 to be changed. Moreover, this allows 3 or more puncture needles to be used also. In addition, the uses of the auxiliary device for puncture needle according to the present invention are not limited to the pullout-puncture needle 30 and the insertion-puncture needle 20 for suturing the abdominal wall A and the gastric wall B, but it may also be used as other puncture needles employed in suturing the other sites in the body.

In an embodiment of the auxiliary device for puncture needle according to the present invention configured as the foregoing, when the puncture needles are used to puncture in a patient's body with the tip portion of the puncture needles positioned at the guide grooves of the auxiliary device placed on the sutured part in the patient's body, and the rotating-sliding contact part is rotated to the surface side of the auxiliary device main body, thereby the puncture needles are prevented from disengaging from the guide grooves of the auxiliary device main body. And, the puncture needles in the foregoing state are pushed against the patient's body; thereby the tip parts of the puncture needles can make punctures in the patient's body. In this case, since the puncture needles move along the guide grooves, the needles can puncture into the body in the appropriate state without displacement.

Moreover, in the event that another puncture needle is used to puncture in the patient's body in parallel to the puncture needle already-punctured into the body, the another puncture needle can be installed in the another guide groove with the rotating-sliding contact part being separated from the surface of the auxiliary device main body once, and then the rotating-sliding contact part is again rotated to the surface side of the auxiliary device main body, thereby both the puncture needles can be positioned in the guide grooves of the auxiliary device main body. Thereby, both the puncture needles can be prevented from disengaging from the guide grooves.

Moreover, with the rotating-sliding contact part remain positioned at the surface side of the auxiliary device main body; the other puncture needle may also be inserted from the upside of the auxiliary device for puncture needle. And, the other puncture needle is pushed against the patient's body; thereby the tip part of the other puncture needle can make a puncture in the patient's body.

In this case, since the other puncture needle also moves along the guide groove, the needle can puncture into the body in the appropriate state without displacement. Moreover, in the event that the positional relationship between the already-punctured puncture needle and the other puncture needle is not appropriate, the puncture auxiliary device can be removed from both the puncture needles to move one of or both the tip parts of the puncture needles so that the positional relationship one another may be adjusted so as to be in the positional relationship in which the surgical suture and the loop body grasping the surgical suture can be easily engaged. As the foregoing, in accordance with the auxiliary device for puncture needle according to the present invention, the puncture operation of the puncture needles can be performed more easily, and at the same time the positional relationships of the plural puncture needles can also be adjusted during the puncture operation.

In another configuration of the auxiliary device for puncture needle according to an embodiment of the present invention, at least the auxiliary device main body out of the auxiliary device main body and the rotating-sliding contact part is formed in a plate-shape, and the guide grooves are formed from one end to the other end of the auxiliary device main body. This allows at least the auxiliary device main body to be easily grasped and the auxiliary device for puncture needle to be manipulated more easily, and at the same time, this further allows the guide grooves to be lengthened, stabilizing the puncture operation when making the puncture.

In yet another configuration of the auxiliary device for puncture needle according to another embodiment of the present invention, a stabilization plate, the bottom surface of which is formed at a plane perpendicularly intersecting with the extending direction of the plural guide grooves, is provided at a portion placed to the skin portion side in the auxiliary device main body. This allows the skin surface and the guide grooves of the auxiliary device for puncture needle to perpendicularly intersect with one another when the stabilization plate is placed to the patient's skin surface during the installation of the auxiliary device for puncture needle in the patient's body, so that the puncture needles can make punctures in the patient's skin portion at an appropriate angle.

In another configuration of the auxiliary device for puncture needle according to yet another embodiment of the present invention, the projecting edge part protruding toward the surface side is formed at a portion opposite to the portion placed at the skin portion in the auxiliary device main body so that the rotating-sliding contact part is positioned inside the projecting edge part when being rotated to the surface side of the auxiliary device main body, and at the same time, the opening side width of the portion constituting the guide grooves in the projecting edge part is larger than the width of the other portion of the guide grooves. This allows the projecting edge part to be a reinforcing part, enhancing the strength of the auxiliary device for puncture needle. Moreover, the opening side width of the portion located on the projecting edge part in the guide grooves is made larger, making the attachment of the puncture needles to the guide grooves easier.

In another configuration of the auxiliary device for puncture needle according to an embodiment the present invention, the confirmation window part for confirming the puncture needle placement is provided at the portion placed to the skin portion side of at least either one of the auxiliary device main body and the rotating-sliding contact part. This allows the puncture operation to be performed while observing the puncture needles passing through the inside of the auxiliary device for puncture needle, making the operation more secure.

What is claimed is:

1. An auxiliary device for a puncture needle assembly having a plurality of puncture needles to secure an organ to an abdominal wall of a patient with a surgical suture, the auxiliary device comprising:
   a main body having an axis and a plurality of parallel guide grooves extending axially from an outer end to an inner end for receiving the plurality of puncture needles and guiding the plurality of puncture needles along the grooves;
   a projecting edge part extending from the main body transverse to the axis of the main body and adjacent the outer end of the plurality of guide grooves in the main body, the projecting edge part having a plurality of guide grooves axially aligned with the plurality of guide grooves formed in the main body and configured for receiving the plurality of puncture needles and guiding the plurality of puncture needles along the guide groove in the projecting edge part; and
   a contact part pivotally attached to the main body for movement between an open position in which the contact part is spaced from the plurality of grooves in the main body part such that the contact part does not contact the plurality of puncture needles when the plurality of puncture needles is received in the plurality of guide grooves in the main body and projecting edge part, and a closed position in which the contact part slidably contacts the plurality of puncture needles when the plurality of puncture needles is received in the plurality of guide grooves in the main body and projecting edge part.

2. An auxiliary device for a puncture needle assembly according to claim 1, wherein the main body and the contact part are each formed in a plate-shape.

3. An auxiliary device for a puncture needle assembly according to claim 1, further comprising a stabilization plate extending from the main body opposite the projecting edge part and configured for placement against the abdominal wall, the plate extending generally perpendicular to the axial direction of the guide grooves such that the needles extend generally perpendicular to the abdominal wall when the plurality of puncture needles are received in the grooves.

4. An auxiliary device for a puncture needle assembly according to claim 3, wherein the contact part is disposed between the projecting edge part and the stabilization plate when the contact part is in its closed position.

5. An auxiliary device for a puncture needle assembly according to claim 1, further comprising a confirmation window adjacent the plurality of grooves in the main body for confirming placement of the plurality of puncture needles.

6. An auxiliary device for a puncture needle assembly according to claim 1, wherein each of the plurality of grooves in the projecting edge part are wider than the plurality of grooves in the main body.

7. An auxiliary device for a puncture needle assembly according to claim 1, wherein in use, the plurality of puncture needles extend generally perpendicular to the patient's skin.

8. An auxiliary device for a puncture needle assembly according to claim 1, wherein the main body and contact part are disposed on opposite sides of the plurality of puncture needles when the plurality of puncture needles is received in the plurality of guide grooves in the main body and projecting edge part.

9. An auxiliary device for a puncture needle assembly according to claim 1, further comprising a hinge pivotally attaching the contact part to the main body, the hinge extending generally parallel to the axis of the main body.

* * * * *